(12) United States Patent
Jansen et al.

(10) Patent No.: US 9,457,296 B2
(45) Date of Patent: Oct. 4, 2016

(54) SEPARATION OF LIQUID COMPONENTS FROM A MIXTURE

(75) Inventors: Rik Jansen, Delft (NL); Arno Willem Frederik Volker, Delft (NL); Peter Van Capel, Delft (NL)

(73) Assignee: Nederlandse Organisatie voor toegepast-natuurwetenschappelijk onderzoek TNO, Delft (NL)

(*) Notice: Subject to any disclaimer, the term of this patent is extended or adjusted under 35 U.S.C. 154(b) by 664 days.

(21) Appl. No.: 13/884,277

(22) PCT Filed: Nov. 10, 2011

(86) PCT No.: PCT/NL2011/050770
§ 371 (c)(1),
(2), (4) Date: Jul. 9, 2013

(87) PCT Pub. No.: WO2012/064191
PCT Pub. Date: May 18, 2012

(65) Prior Publication Data
US 2014/0008304 A1   Jan. 9, 2014

(30) Foreign Application Priority Data
Nov. 10, 2010   (EP) .................................. 10190729

(51) Int. Cl.
*B01D 17/12* (2006.01)
*B01D 17/02* (2006.01)
(Continued)

(52) U.S. Cl.
CPC ............... *B01D 17/04* (2013.01); *B01D 17/12* (2013.01); *C10G 33/02* (2013.01); *C10G 33/08* (2013.01);
(Continued)

(58) Field of Classification Search
CPC ...... B01D 17/04; B01D 17/12; B01D 21/30; B01D 21/302; B01D 21/305; B01D 21/34; C02F 1/02; C02F 1/04; C02F 1/12; C02F 2209/005; C02F 2209/006; C02F 2209/42; C10G 33/02; C10G 33/08; G01B 17/00; G01B 17/02; G01F 23/296; G01F 23/2962; G01N 2291/0222; G01N 2291/02836; G01N 2291/048; G01N 29/02; G01N 29/032; G01N 29/34; G01N 29/348; G01N 29/4418; G01N 29/4472; G01N 2291/104; G01N 2291/105; G01N 2291/106

USPC .......... 210/86, 96.1, 97, 103, 143, 513, 708, 210/739, 744, 748.02, 774, 800, 804; 73/290, 291, 61.43, 61.44; 700/273; 702/50, 54, 55; 703/2, 6, 7, 9
See application file for complete search history.

(56) References Cited

U.S. PATENT DOCUMENTS 5,121,629 A     6/1992   Alba
5,464,529 A *  11/1995   Kozak, III ......... B01D 17/0208
                                                            210/104
(Continued)

FOREIGN PATENT DOCUMENTS

DE        43 05 392 A1     8/1994
WO    WO 2006/098977   *   9/2006

OTHER PUBLICATIONS

Shashank G. Gaikwad et al, "Ultrasonic emulsification: Effect of ultrasonic and physiochemical properties on dispersed phase volume and droplet size", Published in 2008 by Ultrasonics Sonochemistry, vol. 15, pp. 554-563.*
(Continued)

*Primary Examiner* — Joseph Drodge
(74) *Attorney, Agent, or Firm* — Banner & Witcoff, Ltd.

(57) ABSTRACT

Operation of an oil-water separator or other liquid mixture separator is monitored. The separator uses a vessel through which a mixture of different liquid components flows horizontally. A plurality of ultrasound transducers is provided on a wall of the vessel at different heights at a common stage along the direction of the horizontal flow. Ultrasound at a plurality of different ultrasound wavelengths is transmitted through the vessel between transducers and ultrasound arriving transducers is detected. Parameter values of a model are fitted to the detection. A model is used that relates height dependent properties of liquid in the vessel to properties of the detected ultrasound transmission between transceivers, the model comprising at least a fittable parameter of a height dependent droplet size distribution in a least a sub-range of a height of liquid in the vessel. The model relating the droplet size distribution to ultrasound wavelength dependence of the properties of ultrasound transmission. The measured droplet size distribution may be used to determine the route of ultrasound paths and to control demulsification measures.

21 Claims, 5 Drawing Sheets

(51) Int. Cl.
  B01D 17/04      (2006.01)
  B01D 21/30      (2006.01)
  B01D 21/34      (2006.01)
  G01B 17/02      (2006.01)
  G01F 23/296     (2006.01)
  G01N 29/02      (2006.01)
  G01N 29/34      (2006.01)
  G01N 29/44      (2006.01)
  C10G 33/02      (2006.01)
  C10G 33/08      (2006.01)
  G01N 29/032     (2006.01)

(52) U.S. Cl.
  CPC ......... *G01F 23/2962* (2013.01); *G01N 29/032* (2013.01); *G01N 29/348* (2013.01); *G01N 29/4418* (2013.01); *G01N 29/4472* (2013.01); *G01N 2291/0222* (2013.01); *G01N 2291/02836* (2013.01); *G01N 2291/048* (2013.01); *G01N 2291/105* (2013.01)

(56) References Cited

U.S. PATENT DOCUMENTS

| | | | | |
|---|---|---|---|---|
| 2003/0057150 | A1* | 3/2003 | Roudil | B01D 17/0208 210/511 |
| 2003/0117150 | A1* | 6/2003 | Noik | B01D 17/00 324/639 |
| 2006/0058981 | A1* | 3/2006 | Volker | G01N 15/02 702/189 |
| 2006/0265150 | A1* | 11/2006 | Hu | G01N 27/026 702/50 |
| 2010/0089797 | A1* | 4/2010 | Chakka | B01D 17/0208 208/188 |
| 2010/0257931 | A1* | 10/2010 | Partington | G01F 23/2962 73/290 V |
| 2011/0278218 | A1* | 11/2011 | Dionne | B01D 17/04 210/523 |

OTHER PUBLICATIONS

International Search Report—PCT/NL2011/050770—Mailing Date: Feb. 14, 2012.

Alba F et al: "Acoustic spectroscopy as a technique for the particle sizing of high concentration colloids, emulsions and suspensions", Colloids and Surfaces A: Physicochemical and Engineering Aspects 19990815 Elsevier N L, vol. 153, No. 1-3, Aug. 15, 1999, pp. 495-502.

Jaworski A J et al: "On-line measurement of separation dynamics in primary gas/oil/water separators: Challenges and technical solutions—A review", Journal of Petroleum Science and Engineering, Elsevier, Amsterdam, NL, vol. 68, No. 1-2, Sep. 1, 2009, pp. 47-59, XP026419270, ISSN: 0920-4105, [retrieved on Jun. 21, 2009].

Faisal et al., "Multi-interface Level Sensors and New Development in monitoring and Control of Oil Separators" (Sensors by MDPI, No. 6, 2006, 180-189).

Ismail et al, "Tomography for multi-phase flow measurement in the oil industry" (Elsevier, Flow Measurement and Instrumentation, No. 16, 2005, 145-155).

* cited by examiner

SEPARATION OF LIQUID COMPONENTS FROM A MIXTURE

CROSS-REFERENCE TO RELATED APPLICATIONS

This application is a U.S. National Stage application under 35 U.S.C. §371 of International Application PCT/NL2011/050770 (published as WO 2012/064191 A1), filed Nov. 10, 2011, which claims priority to Application EP 10190729.3, filed Nov. 10, 2010. Benefit of the filing d of each of these prior applications is hereby claimed. Each of these prior applications is hereby incorporated by reference in its entirety.

FIELD OF THE INVENTION

The invention relates to a method of controlling a separator for separating liquid components from a mixture, such as an oil-water mixture for example, a method of monitoring operation of such a separator, a method of determining a phase distribution of fluid in a vessel, a separator and characterization and control systems for performing the methods.

BACKGROUND

Oil is often produced as part of an emulsion of water and oil. An oil water separator may be used to separate the oil from the water. In one embodiment such a separator comprises an elongated vessel, through which the oil-water mixture flows horizontally to a height-controllable weir on one side of the vessel. During the time interval in which a volume element of the oil water mixture flows through the vessel, droplets in the emulsion coalesce. Various measures may be applied in the vessel to promote removal of the emulsion, such as heating, application of electrostatic fields, adding agents to reduce oil-water surface tension etc. Conventionally, a predetermined flow speed is selected so that there is always sufficient time for substantially all droplets to coalesce in the time interval in which a volume element of the oil water mixture flows through the vessel. As a result a water body forms in the vessel at the bottom and an oil body forms at the top, possibly with a gas phase above the oil. The height of the weir is adjusted according to the height of the separation between the bodies of water and oil, in order to collect an oil fraction free of water and/or waste water that is substantially free of oil.

In order to be able to adjust the weir height to the height of the separation between oil and water, a measuring system is used to measure the height of this separation. Various solutions have been proposed for this purpose.

From an article by Bukhari et al, published in Sensors 6 (2006) pages 380-389 and titled "Multi-interface Level Sensors and New Development in Monitoring and Control of Oil Separators" it is known to measure oil water separation levels by using a series of ultrasonic transmitter-receiver pairs at different heights along vertical walls of a separator vessel. Each pair can be used to determine the speed of sound or sound absorption at a different level, from which it can be determined whether oil or water is present at that level. It is also known to provide such transmitter-receiver pairs at different heights on a probe that is inserted in the separator vessel. This makes it possible to overcome the problem that measurements at individual heights with ultrasound transducers on the walls of a vessel without vertical walls are not possible (because ultrasound usually radiates only in a direction normal to the wall). However, transmitter-receiver pairs at many different heights may be needed to obtain sufficient height resolution.

Bukhari et al also describe a method that works with a single receiver-transmitter pair on the wall of a vessel with rounded cross-section. In this method a transmitter and receiver are located at the bottom of the vessel, to transmit and receive back ultrasound through the emulsion above the bottom. From the time delay of received reflections from interfaces between different phases in the vessel the levels of these interfaces can be estimated. However, the oil water interface produces only a weak reflection, which is hard to detect. When an emulsion is present between the oil and the water, it is even more difficult to obtain useful measurements.

Form an article by Jaworski et al, published in the Journal of Petroleum Science and Engineering 68 (2009) pages 47-59, and titled "On-Line measurement of separation dynamics in primary gas/oil/water separators: Challenges and technical solutions—A review", it is known to use tomography for monitoring heterogeneous mixtures in separators. The article describes an example of electrical capacitance tomography, using capacitor plates on the periphery of the separator and measurement of capacitance between respective pairs of plates. The article also describes the possibility of using gamma-ray tomography or combinations of multiple modes of tomography. As noted by the article appropriate reconstruction algorithms may be used to obtain a cross-sectional image of the distribution of the measured property such as the dielectric constant or resistivity, but no specific algorithm is described. Conventionally for gamma rays, tomography involves back-projection, identifying paths between each pair of electrodes, and assigning contributions to the fluid properties at positions along the path in proportion to the measured capacitance between the electrodes.

Compared to level sensing tomography has the advantage that an image of a measurable property such as electrical polarizability or gamma ray absorption as a function of position can be obtained without requiring transmitters and receivers at equal height that "see" each other. When the expected value of the measurable property in the tomographic image is different for water and oil, the tomographic image can be used to control the height of the weir, by setting it to the height in the image where the value of the measurable property substantially reaches the expected value for oil.

Ultrasound tomography is known per se, and it could be applied to a separator vessel, by providing for ultrasound transducers. The speed of sound in oil and water is different, so that measurement of ultrasound travel times can be used to distinguish oil and water bodies. When ultrasound tomography is used, there is no need to provide equal height pairs of ultrasound transmitters and receivers at a large number of heights along the vessel.

However, it has been found that sometimes the results obtained with ultrasound tomography in a separator vessel still may still be inaccurate. It has been found that this occurs especially when there is a substantial height of emulsion left at the measurement stage. When equal height pairs of transducers are used, this may have the effect that the pairs in the emulsion range produce results that cannot clearly attributed to either water or oil. For tomography with ray paths at an angle to the horizontal the result is worse, as it also makes the determination of the limits of the water and oil bodies inaccurate. Of course these problems are normally avoided by performing the ultrasound measurements near the weir and using a flow speed that ensures sufficient time for removing the emulsion.

Determination of the droplet size distribution in an emulsion from the frequency dependence of ultrasound attenuation is known from an article by F. Alba et al., titled "Acoustic spectroscopy as a technique for the particle sizing of high concentration colloids, emulsions and suspension". Alba et al. show that the size distribution of droplets in an oil-water emulsion can be determined by fitting the parameters of a model to measured frequency dependent ultrasound attenuation, using a model that predicts the frequency dependent attenuation as a function of parameters of the droplet size distribution.

In principle, Alba et al. make it possible to measure the cumulative droplet size distribution in a vertical column with an oil-water mixture, by measuring ultrasound wavelength dependent attenuation along a vertical ray path. But in oil water separator vessel, wherein gas is present above the mixture, reflections from the gas-liquid interface make such measurements. Alba et al. do not consider determination of position dependent droplet size distribution. Sensing horizontal transmission at discrete heights would require many transmitter reducer pairs, and is impossible altogether when the vessel has a rounded wall and ultrasound propagates normal to the wall. Alba et al. do not consider effects of inhomogeneity on the part of the emulsion that is traversed by ultrasound in the case of rays at a non-zero angle to the variation of the distribution, or application of determination of droplet size distribution to control of an oil-water separator.

SUMMARY

Among others it is an object to provide for a more reliable method of characterizing a fluid in a separator containing a mixture of different liquid components, such as oil and water.

A method of monitoring operation of a liquid mixture separator, according to claim 1 is provided. The separator comprises a vessel through which a liquid mixture such as an oil water mixture flows horizontally and a plurality of ultrasound transducers on a wall of the vessel at different heights at a common stage along the direction of the horizontal flow. The method comprises transmitting ultrasound through the vessel from at least first part of the transducers and detecting ultrasound arriving at at least a second part of the transducers for a plurality of ultrasound wavelengths. The detected ultrasound transmission is used in a parameter fitting process. Parameter values of a model are fitted to properties of ultrasound transmission between transceivers. A model is used that relates height dependent properties of liquid in the vessel to the properties of ultrasound transmission. The model has a fittable parameter of a height dependent droplet size distribution in a least a sub-range of a height of liquid in the vessel.

By using a plurality of different ultrasound wavelengths, combined with fitting a height dependent model it is made possible to determine properties of an emulsion distinguish between emulsions in the vessel with different height dependent droplet size distributions. A parameter of such a distribution may be used to control the application of demulsification measures. Thus, excess use of chemicals or excess power dissipation for demulsification can be avoided. Demulsification measures may include adding de-emulsifier compound to the liquid mixture, heating the mixture, or applying an electrostatic field to promote fusion between droplets.

In embodiment an intensity of the demulsification measures may be adapted dependent on said fitted value of the parameter for example. The intensity of the demulsification measures may be increased by lowering the flow speed of the liquid mixture in the separator vessel, adding more de-emulsifier compound, applying more heating, or higher electrostatic fields. The intensity may be increased for example according to estimate of the number of droplets below a predetermined size, the estimate being derived from the fitter parameter. Thus higher intensity demulsification may be applied when there are more small droplets, for which relatively more energy is needed for coalescence. Different types of demulsification measures or different combinations of demulsification measures may be selected dependent on said fitted value of the parameter, for example by activating electrostatic demulsification when it is detected that the mixture comprises water droplets in oil, or adding chemicals only if a number of droplets exceeds a threshold. In another embodiment a selected height dependence of the demulsification measures may be applied dependent on the value of the fitted parameter. Use of droplet size parameters determined with transducers upstream of a stage wherein the demulsification measures are operational, makes it possible to use feed-forward control, preventing losses involved with response time of feedback loops that perform control based merely on measurement of the presence of remaining emulsion at the end of the separator vessel.

It has been found that the identification of a sub-range range with ultrasound transmission parameter values that can be classified as belonging to an oil water mixture can improve the reliability of the operation of the separator. In an embodiment a model may be used that has parameters defining the vertical levels (heights) between bodies of water and oil and an intermediate emulsion. The mode may comprise one or more parameters defining a gradient between these levels. In this way ultrasound ray paths with non-zero curvature dependent on the oil water ratio gradient may be accounted for in the determination of droplet size distribution along ray paths. This improves the reliability of the determination of the separation levels in the separator vessel. The parameters of the model may include a parameter defining a transition height between an oil droplet in water emulsion and a water droplet in oil emulsion.

In an embodiment an oil-water separator according to claim 10 is provided. In a further embodiment the oil-water separator may have transducers clamped on to a wall of the separator vessel. Because model fitting is used, such clamp-on transducers can be used even if the vessel has rounded walls, so that the opening angles of sound transmission into the interior from the wall may exclude the horizontal.

In an embodiment a computer program product comprising a program of instructions for performing the method is provided. The computer program product may be a machine readable disk (optical or magnetic for example) storing the program, or a computer readable semi-conductor memory storing the program. The computer program product may be a signal carrying information that defines the program.

BRIEF DESCRIPTION OF THE DRAWING

These and other objects and advantageous aspects will become apparent from a description of exemplary embodiments, using the following figures.

DETAILED DESCRIPTION OF EXEMPLARY EMBODIMENTS

Figure 1A:
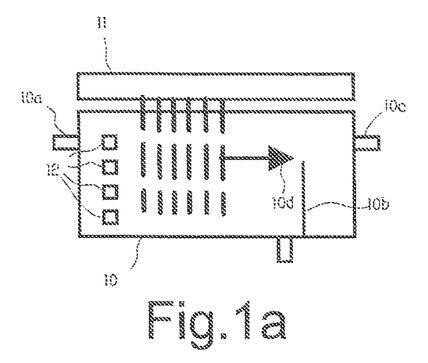
FIG. 1a-c illustrate a separator

FIG. 1a illustrates a separator vessel 10, with an inlet 10a, a weir 10b, and an oil outlet 10c. In one embodiment separator vessel 10 may have a length of ten meter and a diameter of three meters, but of course variations of this size may be used. The flow direction is shown by an arrow 10d. A controllable emulsion reducer 11 is schematically indicated, a flow stage where emulsion reduction is operational being indicated by dashed lines (emulsion reduction by emulsion reducer 11 may be operational at more stages than the one shown). A number of ultrasound transducers 12 is shown on the wall of separator 10, on a vertical section of separator 10 at a flow stage upstream of the operational stage of emulsion reducer 11, adjacent inlet 10a.

Figure 1B:
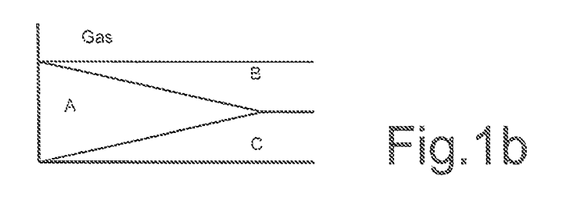

FIG. 1b illustrates a height distribution of fluid in separator 10 as a function of position along the flow direction. Near inlet 10a, the entire height may be substantially occupied by an emulsion A of water and oil and gas. Reduction of the amount of emulsion (demulsification) occurs inherently in the course of time while when the oil-water mixture is in the separator vessel 10. This translates into a reduced height of emulsion as a function of position. Downstream, a body of oil B and a body of water C emerge. The height of the emulsion A diminishes along the flow direction, so that the levels of the transitions from these bodies B and C with the emulsion C converge. Ideally the height of the emulsion A becomes zero before weir 10b.

Emulsion reducer 11 is provided to speed up the rate of demulsification and/or the flow speed and thereby the duration of the time interval that is available for demulsification in separator vessel 10. The combination of the rate and the duration will be referred to as the intensity of demulsification. Emulsion reducer 11 may be configured to control the flow rate through separator 10, an electrostatic field in separator 10, heating and/or supply of demulsifier compound to the fluid that is processed by separator 10. Accordingly, emulsion reducer 11 may comprise a controllable valve at inlet 10a, a voltage generator and electrodes at the flow stage where emulsion reduction is operational, a heater at that flow stage and/or a controllable supply of emulsifier compound before and/or in that flow stage. The intensity of demulsification in separator vessel 10 increases with reduction of the flow rate, applying more electric voltage, applying more heating and/or adding demulsifier compound at a higher rate. The rate of demulsification may depend on emulsion properties, such as droplet size. Some demulsification measures are effective only for some forms of emulsion. For example electrostatic fields are not effective to demulsify oil droplets in water, although they work well against water droplets in oil.

It is desirable to minimize the intensity of demulsification, e.g. to realize a greater flow speed, use less electrical power and/or expend less demulsifying agent. No more intensity is needed than is sufficient to ensure that the emulsion A has been removed when the oil-water mixture travels reaches weir 10b.

The minimum sufficient intensity of demulsification depends on internal emulsion properties such as droplet size, the type op droplets (oil droplets in water, water droplets in oil) and heights of water droplet in oil and oil droplet in water fractions. For example, as a relatively higher energy is needed to overcome the surface energy of small droplets, the required intensity of demulsification for removing oil in smaller droplets is higher than the intensity needed for removing the same number of larger oil droplets, even though in this case the larger droplets lead to a greater fraction of oil in the emulsion. The same goes for smaller and larger water droplets.

Figure 1C:
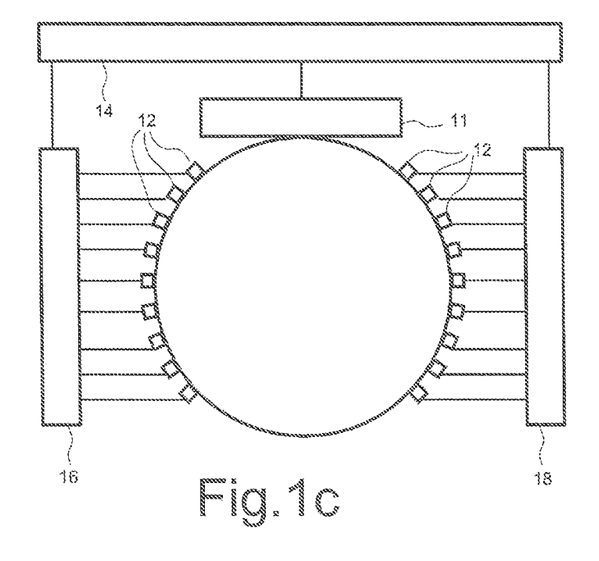

The system comprises a controller 14, a signal generator 16, receiver 18 and emulsion reducer 11. A plurality of ultrasound transducers 12 is shown located at different positions along the periphery of the cross-section of separator 10. Any number of transducers 12 may be used, for example twenty on each side of separator (forty in total) and preferably at least ten transducers 12 on each side of separator 10. Preferably clamp-on transducers are used, i.e. the wall of separator vessel may run on uniformly along positions where transducers 12 are located and where not, the transducers being placed on this uniform wall. Controller 14 has control outputs coupled to signal generator 16 and emulsion reducer 11 and inputs coupled to receiver 18. Signal generator 16 has outputs coupled to transducers 12. Receiver 18 has inputs coupled to transducers 12.

Figure 2:
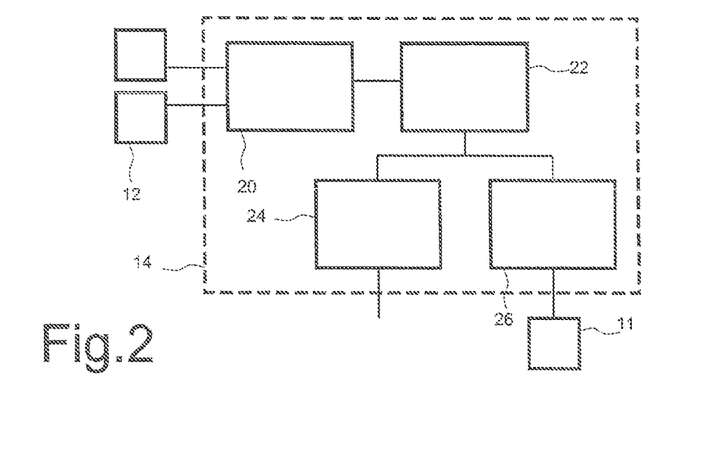
FIG. 2 shows a system architecture

FIG. 2 shows an architecture of controller 14. Controller 14 comprises an ultrasound measurement control module 20, a signal processing module 22, a weir control module 24 and a demulsification control module 26. Measurement control module 20 has inputs and outputs coupled to signal generator 16 and receiver 18. Signal processing module 22 has an input coupled to measurement control module 20 and outputs coupled to weir control module 24 and demulsification control module 26. Weir control module 24 is coupled to a control input (not shown) of weir 10b.

Demulsification control module 26 has an output coupled to a control input of emulsion reducer 11. The control input may control voltages applied to electrodes in separator vessel 10 and/or a dose control valve between a supply vessel with a demulsifying compound and separator vessel 10, and/or an inlet valve of separator vessel 10 to control flow speed of the oil-water mixture in separator vessel 10 and/or an outlet valve of separator vessel 10 to control this flow speed.

Preferably, a control strategy is used wherein the intensity of demulsification measures is kept at a minimum sufficient level.

An embodiment has been shown wherein the set of ultrasound transducers 12 is located in a vertical section of separator 10 adjacent inlet 10a, i.e. at a stage of the horizontal flow in advance of the flow stage where demulsification measures have effect. In this embodiment, demulsification is controlled by feed forward steering, at least one operational stage of demulsification lying downstream from the transducers 12 that are used to control it (between these transducers 12 and weir 10b). Alternatively or additionally, a set of ultrasound transducers may be located in a vertical section of separator 10 adjacent weir 10b, at a stage of the horizontal flow downstream from the flow stage where demulsification measures have effect. In this embodiment, feed-back control of demulsification may be used. Feedback has the advantage that the effect of demulsification measures can be confirmed. But feedback has the disadvantage that an amount of uncorrected flow will occur before the feedback can take effect. Feed forward steering can avoid this. But for feed forward steering it is desirable to know parameters of the droplet size distribution that affect the rate of demulsification, so that the intensity of demulsification can be adapted to the drop-let size distribution in advance.

Figure 3:
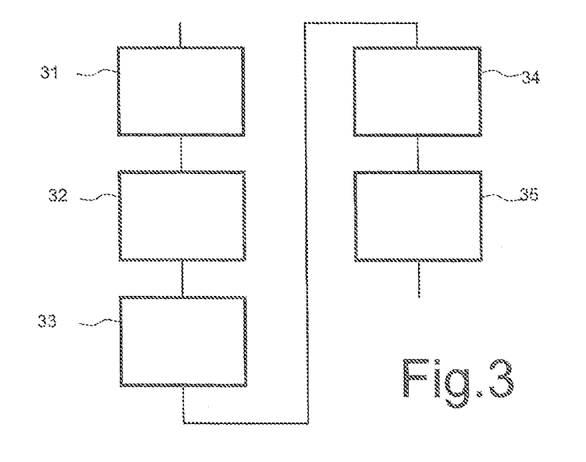
FIG. 3 shows a flow chart of signal processing

FIG. 3 shows a flow-chart of signal processing. In a first step 31, ultrasound measurement control module 20 successively selects different transducers 12. For each selection transducer, ultrasound measurement control module 20 uses signal generator 16 and receiver 18 and transducers 12 to measure ultrasound travel times and attenuations between respective pairs of transducers 12 for a plurality of ultrasound frequencies.

In one embodiment ultrasound measurement control module 20 may do so by causing signal generator 16 to apply a plurality of pulse signals, containing oscillations at respective different frequencies to the selected transducer 12. Ultrasound with frequencies from a frequency range from 20 kHz to 5 MHz may be used for example. Ultrasound measurement control module 20 causes receiver 18 to detect acoustic signals in response to acoustic excitation by other transducers 12, or at least to the other transducers that are located on the half of the wall opposite the half of the wall on which the selected transducer 12 is located.

Pulse excitation may be used, however, it should be appreciated that other types of measurement may be used. For example using pulses that contain a mix of oscillations at different frequencies, or broadband pulses. Instead of pulses, frequency swept or modulated signals may be used, the travel time and attenuation of different frequencies being determined from the received signal phase and strength at different time points of the sweep.

In a second step 32, signal processing module 22 receives the measurements of the received acoustic signals. In this step signal processing module 22 may determine ultrasound travel times and attenuation as a function of ultrasound wavelength (frequency), for example, but instead the response signal as a function of time may be sampled, which implicitly contains information about travel time and attenuation. In a third step 33, signal processing module 22 performs model fitting to determine parameters of a model of the properties of the fluid in separator 10 as a function of height.

The Model

The parameters include parameters defining the heights of a plurality of levels that separate successive sub-ranges of the height of separator vessel 10. In one example, parameters defining heights h1, h3 of a first and second level may be provided, corresponding to h1—a water to oil-in-water emulsion transition level,
h3 a water-in-oil emulsion to oil transition level.

The difference between these heights corresponds to a sub-range in which emulsion is present. In addition the model may specify a third height h2 of an oil-in-water emulsion to a water-in-oil emulsion transition level. Furthermore, the model may specify a fourth height h4, of the liquid-gas interface.

The model may have further parameters to describe a dependence of properties of the emulsion as a function of height in separator 10 between these levels. These properties may include one or more parameters of droplet size distribution between the levels h1 and h3. The model assumes that the properties are a function of height only and are independent of position in a horizontal direction transverse to the direction of flow. Furthermore, the model defines relations between values of the parameters of the model and values of predicted response signals. An embodiment will be described wherein the relations the model may give an expression for predicted travel time and attenuation of ultrasound transmitted between pairs of transducers 12, but instead an expression for the response signal as a function of time may be provided.

The model may define the speed of sound as a function of height.

$C(h)$

The speed of sound $C(h)$ may be taken constant below the water to oil-in-water emulsion transition level h1 and above the water-in-oil emulsion to oil transition level h3 up to the gas-oil interface and variable between the levels h1-h3. The speed of sound in water may have a predetermined value and the speed of sound in oil may be a variable parameter of the model, dependent on oil composition. The model may comprise coefficients that define the speed of sound as a continuous function of height. A combination of values at discrete locations and an interpolation function may be used for example, or values of coefficients a0, a1, a2 . . . of a polynomial that represents the speed of sound in the emulsion part of the height:

$$C(h)=a0+a1*h+a2*h^2\ldots$$

Typically, the speed of sound is related to the ratio of oil and water in the emulsion, so that the level of separation between oil in water and water in oil emulsion is not relevant for the sound speed model and the coefficients a0, a1, . . . relate directly to said ratio. Alternatively, the model may have parameters that define the oil-water ratio as a function of height.

Furthermore, the model may define the attenuation coefficient $A(f;h)$

As a function of height h and frequency f the attenuation coefficient depends on the droplet size distribution in the emulsion. The wavelength dependence of attenuation is affected by scattering. An emulsion with droplets of a single size will scatter ultrasound with a wavelength close to the droplet diameter more than ultrasound with a wavelength that is substantially different from the droplet diameter. Of course a practical emulsion in a separator contains a mix of different droplet sizes, in numbers according to the droplet size distribution. In this case the attenuation coefficient can be modeled as a sum of frequency dependent contributions $Ao(f;d)$ for different droplet diameters d, weighted by the droplet size distribution $N(d)$.

$$A(f)=\text{Sum } N(d)*Ao(f;d)$$

Droplets are absent below the water to oil-in-water emulsion transition level and above the water-in-oil emulsion to oil transition level. For these height ranges substantially height independent attenuation coefficients may be assumed. The model may define the frequency dependent attenuation coefficient as a function of height in the emulsion range. Parameterized frequency dependent functions may be used, which depend on parameters that in turn depend on height. Polynomial coefficients may be used to define the height dependence of these parameters.

Alternatively, the model may be expressed in terms of droplet size distribution in terms of parameters of a parameterized function $N(d)=g(d;b)$ dependent on parameters "b". The model may comprise coefficients q0, q1, . . . of polynomials that define these parameters b as a function of height in a water in oil emulsion part and an oil in water emulsion part of the height:

$$b = q0 + q1*h + q2*h^2 + \ldots$$

Although specific examples of parameters of the model have been given, it should be appreciated that different ways of defining a model may be used. For example, values of speeds of sound and parameters of droplet size distributions at discrete heights may be used, together with an interpolation method for deriving values at other heights.

Figure 4:
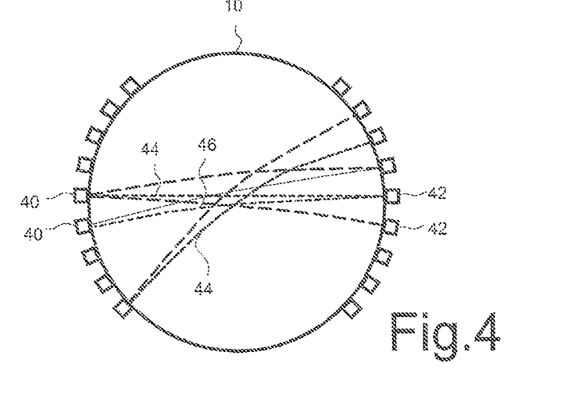
FIG. 4 shows transducer locations and ray paths
Figure 5:
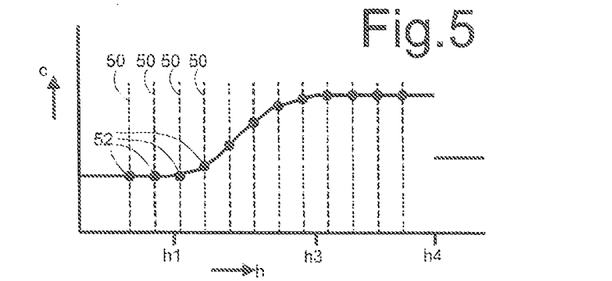
FIG. 5, 5a show a graph of modeled sound speed versus height
Figure 5A:
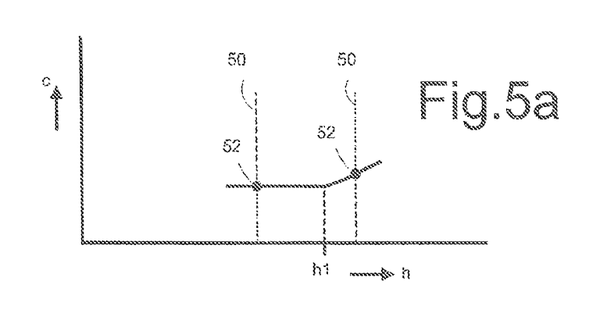

FIG. 4 shows examples of ray paths 44, 46, 48 between transducers 40, 42. As can be seen ultrasound rays are used that radiate in a direction normal to the wall of separator vessel 10, or a near normal direction. For most ray directions beyond an opening angle range no reliable measurements are possible. In many cases each transmitting transducer 40 can reach a plurality of receiving transducers 42. Optionally additional ray paths may be used that run laterally through the wall of vessel 10 from the transducers 12 before radiating into the interior of vessel and/or run laterally through the wall after passing through the vessel 10 before reaching a transducer 12. Such a form of transmission gives rise to the problem that the start and end of the ray path through the interior of vessel 10 do not correspond directly with the position of the transducers on the wall of vessel 10. That this type of transmission applies can be detected from the pair of transducers between which transmission is measured: it occurs between pairs that are not in each others opening angle. To use the measured transmission signal between such transducers a ray path is computed using information about the ultrasound transmission properties of the wall of vessel 10 (its thickness and bulk speed of sound) and the modeled properties of the liquid in separator vessel 10. Also there may be a relatively small contribution to the transmission between transducers that are in direct "sight" of each other, but this can usually be neglected or ignored by using only the transmission in a time window that corresponds to direct transmission. A time window may be used also to exclude transmission signal parts due to transmission through the wall only. FIG. 5, 5a show graphs of modeled sound speed versus height in vessel 10. At different heights 50 different modeled speed values 52 may hold. Ray paths 44, 46, 48 that are not strictly horizontal or vertical will be curved, or even show ray breaking when the speed of sound depends on height or even shows a discontinuity as a function of height.

The travel time and attenuation between transducers 12 at mutually different heights h(i), h'(j) depends on the ultrasound ray path between the transducers. The ray path bends due to sound speed gradients. In an embodiment, the model provides for a computation of the ray path from the modeled height dependence of the speed of sound C(h). Bending may be computed according to Snellius's law, using the sound speed gradient. Typically the ray path is the path that realizes the shortest travel time. The model may comprise a module that is configured to perform a search for a ray path between the transducers 12 that minimizes travel time.

The effect of the parameters on the travel times T(i,i') measured is an integral (a sum) of contributions that are inversely proportional to the speed of sound C(h) along the ray path. The effect of the parameters on the frequency dependent path attenuation between transducers 12 is a sum of attenuation coefficients along the bent ray path.

Approximate height dependences of attenuation coefficients and speeds of sound could be determined by means of tomographic techniques. In one embodiment, tomography may involve back-projection of observed transmission measurements between a pair of transducers 12 to the ray path between the transducers 12. Back-projection typically involves notionally distributing the measured travel time or attenuation between a pair of transducers 12 along a line between the transducers 12

In another solution back-projection of observed transmission measurements between a pair of transducers 12 to height ranges between the transducers 12 is used. This involves notionally distributing the measured travel time or attenuation between a pair of transducers 12 over height sub-ranges. The ray path between the transducers 12 is determined, and the travel time and attenuation per unit length segment of the line distributed over the height ranges in proportion to the length fractions of the ray path in the different height sub-ranges.

A better resolution, especially near the heights h1, h3 of the emulsion and water and oil can be obtained by using a model that has these heights as parameters.

Model Fitting

In third step 33, signal processing module 22 computes parameters of the model by means of model fitting, e.g. by a feedback process wherein the parameters of the model are adjusted dependent on a difference between the measured and the parameter dependent predicted response, at least on average in a direction of parameter adjustment that reduces the difference. In an embodiment adjustment is continued iteratively until the feedback has settled to a set of values that results in predicted ultrasound response signals (e.g. travel times and path attenuations) between pairs of transducers 12 with a stable, zero or small, deviation from the observed response signals.

The model fitting divides the height of liquid in separator vessel 10 in successive sub-ranges, delimited by the heights h1, h3 and optionally h2, according to the ultrasound transmission properties assigned to the liquid in these height sub-ranges. One model fitting process may be used for both sound speed and attenuation, wherein the parameters are adjusted to fit a set of measured time dependent response signals between respective transducer pairs. In this way both parameters that are relevant for travel time and parameters that are relevant for attenuation may be fitted together.

In an alternative embodiment a first and second model fitting process may be executed. The first model fitting process fits the model parameters that are relevant for travel time (speed of sound or oil water ratio), optionally independent of ultrasound wavelength. The second model fitting process fits the model parameters that are relevant for attenuation to the wavelength dependence. Before the first and second model fitting process a set of measured travel times and a set of ultrasound frequency dependent attenuation values may be determined first from the set of measured time dependent response signals. The first model fitting process fits the parameters to set of the measured travel times, and determines the ray paths between the pairs of transducers. The second model fitting step fits the parameters that are relevant for attenuation to the set of measured attenuations.

It should be appreciated that the use of a combination of response signals measured for ray paths at different angles to the horizontal makes it possible to derive information about the height dependence of the speed of sound at a higher resolution, or in a more accurate approximation than by using only horizontal ray paths. When a model is used that defines the height dependence of the speed of sound as a function that has values for all heights between the heights of the transducers as a function of model parameters, the ray path and the corresponding travel times can be predicted dependent on the parameter values. Accordingly parameter values can be selected that best fit the measured travel times. This makes it possible to determine parameters such as heights of interfaces between the heights of transducers, which can be used to control separation and/or to estimate more accurate values of oil flow parameters.

Furthermore, it should be appreciated that fitting parameters to the set of measured ultrasound frequency dependent attenuations, or fitting parameters to the set of time dependent response signals that implicitly contains information about frequency dependent attenuation, provides for extraction of information that cannot be derived using travel time only.

The properties of the frequency dependent attenuation coefficient as a function of height differ from the speed of sound in that they depend on the interface height h2 at which the emulsion changes from an oil droplet in water emulsion to a water droplet in oil emulsion. Unlike the speed of sound in the emulsion, which depends mainly on the ratio of oil and water, the attenuation coefficient for a given ultrasound frequency depends on the concentration of droplets with diameters comparable to the wavelength of the ultrasound. At the interface from an oil droplet in water emulsion to a water droplet in oil emulsion, this concentration of droplets with specific diameters changes, which results in changes in the attenuation coefficient at certain frequencies dependent on the diameters. This means that frequency dependent attenuation coefficient can be used to determine the height h3 of the interface from an oil droplet in water emulsion to a water droplet in oil emulsion.

When there is a jump in path attenuations at some frequency measured for adjacent pairs, a comparison between frequency dependent path attenuations measured with adjacent equal height pairs may suffice to detect that the interface height h2 lies in a range of heights between the heights of these adjacent pairs. If only a water droplet in oil or only an oil droplet in water emulsion is present between the oil and water bodies, no interface height h2 at which a significant jump in path attenuation will be distinguishable. In this case, the nature of the single emulsion can be determined from the gradient of the particle size distribution: signal processing module 22 may assign the emulsion to be a water droplet in oil or an oil droplet in water emulsion if the average droplet size decreases or increases from the water body to the oil body respectively.

Figure 6:
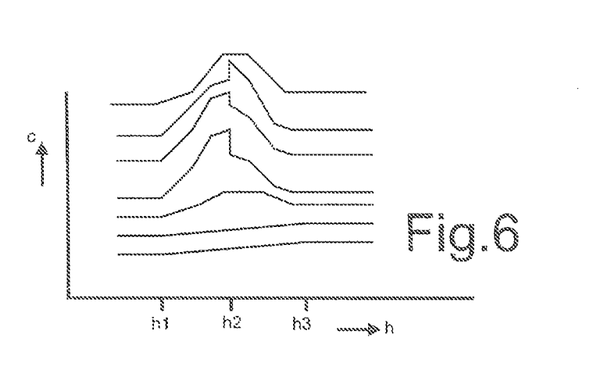
FIG. 6 shows a graph of modeled frequency dependent attenuation versus height
Figure 6A:
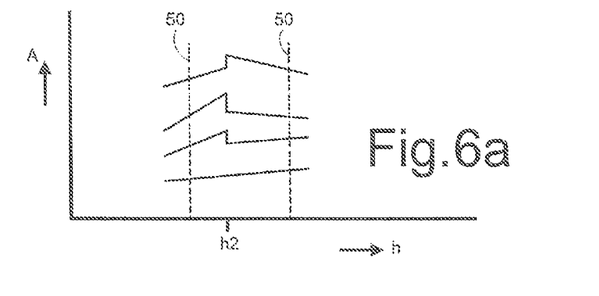
FIG. 6a shows frequency dependent attenuation in detail

FIG. 6 qualitatively illustrates modeled dependence of the attenuation coefficient on height as for a number of ultrasound frequencies. FIG. 6a illustrates dependencies in detail. Typically, the attenuation coefficient is higher in the height range where an emulsion is present, due to scattering of ultrasound from droplets. The droplet size distribution determines the frequency dependence: if the density of droplets with diameters in a certain value range is high, this increases attenuation of ultrasound with wavelengths in that value range. At the height h2 of the oil droplet in water to the water droplet in oil range there is typically a jump in the attenuation coefficient for a number of frequencies. The jump is most pronounced for ultrasound with wavelengths that correspond to diameters for which the droplet density in the oil droplet in water to the water droplet in oil differs most markedly. For different emulsions these wavelengths and the sizes of the jumps may vary, dependent on specific emulsion properties. As illustrated qualitatively in FIG. 6a, a model may be used according to which the frequency dependent attenuation coefficient locally varies linearly on height, except at the heights of the interfaces, such as the height h2 of the oil droplet in water to the water droplet in oil interface. The modeled dependence on opposite sides of the interfaces may be extrapolations of the adjacent height dependence.

Using this model, the vertical position h2 of the intra-emulsion interface can be determined by measuring frequency dependent path attenuation between pairs of transducers at equal height, determining adjacent pairs (j,j'), (j+1, j'+1) of equal height transducers on opposite sides of the height h2 of the emulsion interface, measuring the path attenuation between transducers i, i'+1 at adjacent different heights on the opposite sides, and selecting a height value h2 that results in a predicted path attenuation equal to the measured frequency dependent path attenuation, assuming independent extrapolations of frequency dependent attenuation coefficients on both sides of that level.

The estimate of the frequency dependent path attenuation between transducer heights between which there is no interface can be refined as well, using path attenuation measurements between transducers k, k'+1 at adjacent heights, as described for the speed of sound.

In the preferred overall fitting approach measurements of travel time and frequency dependent path attenuation between arbitrary transducers at non-adjacent heights are added and values of the model parameters are determined that result in a best fit, such as a minimum least square error between measured travel times and frequency dependent path attenuations and predictions of these quantities based on the parameter values. Instead of piecewise linear models of the height dependence other models may be used.

What should be appreciated is that the use of a combination of frequency dependent path attenuations measured for ray paths at different angles makes it possible to derive information about the height dependence of droplet size at a higher resolution, or in a more accurate approximation than by using only horizontal ray paths. When a model is used that defines the height dependence of the attenuation coefficient as a function that has values for all heights between the heights of the transducers as a function of model parameters. The path attenuation along the ray path can be predicted dependent on the parameter values. Accordingly parameter values can be selected that best fit the measured path attenuations. This makes it possible to determine parameters such as a height of an oil-droplet emulsion, water droplet emulsion interface between the heights of transducers, and/or to estimate more accurate values concentrations of different droplet sizes, which can be used to control demulsification measures.

Application to Control of Demulsification and Weir Height

The estimated model parameters may be used to control demulsification. Returning to the process of FIG. 3, in a fourth step 34, demulsification control module 26 uses parameters of the model to control the intensity and/or the selection of emulsion reduction measures, or subset of emulsion reduction measures that will be used. Emulsion reduction may be intensified for example by reducing the flow rate of the fluid through separator, heating to raise the temperature of the fluid, adding emulsifying compound at a higher rate and/or increasing electrostatic fields in separator 10. The type of applied measures and their intensity may be adapted in response to variations in properties of the emulsion. In an embodiment, a demulsification measure may be applied in a selectable height sub-range that is selected dependent on the measured vertical position of the emulsion.

In an embodiment demulsification control module 26 selects the type of emulsion reduction measures automatically dependent on the type of droplets. Control module 24 may be configured to switch on electrostatic demulsification only when more than a predetermined height of the emulsion is found to contain water droplets in oil for example, or to select between introducing different demulsifying compounds dependent on the type of emulsion.

In an embodiment demulsification control module 26 selects height sub-range in which one or more emulsion reduction measure is or are applied, or respective sub-ranges for respective demulsification measures. In this embodiment emulsion reducer 11 is configured to apply demulsification measures in a height selective way, for example, by providing respective electrodes in respective sub-ranges of the height of separator vessel 10 and applying electrostatic fields or heating only using selected electrodes. Emulsion reducer 11 may have a plurality of outlets at different heights in separator vessel 10 for introducing demulsifying compounds at the different heights, and valves to outlets may be opened selectively.

Figure 7:
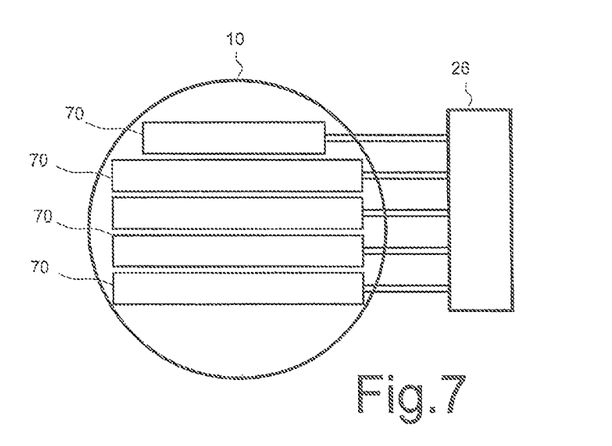
FIG. 7 shows a separator with a plurality of sets of electrodes

FIG. 7 shows an embodiment wherein a plurality of sets of independent electrodes 70 are provided at mutually different heights in separator 10. In this embodiment demulsification control module 26 may be configured to select the field strengths in the different sets of electrodes dependent on the estimated location of the emulsion.

Demulsification control module 26 may be configured to switch off the field for electrodes above and below the heights h3 and h1 for example. In another example, demulsification control module 26 may be configured to adjust the fields at different heights according to estimated indicators of the concentration of small droplet sizes at the different heights within which of these set of electrodes electric field.

In an embodiment demulsification control module 26 is configured to increase the intensity of emulsion reduction measures with increased droplet size and to decrease the intensity, if possible, with decreased droplet size. Demulsification control module 26 may be configured to determine an estimate of the number of droplets below a predetermined size and to adjust the intensity according to this estimated number. The estimate may be derived from the parameters of the droplet size distribution, such as the average, standard deviation and amplitude of the droplet size distribution as a function of height (or for a single height, or height averaged average, standard deviation and amplitude if the height dependence is not significant).

Coalescence of droplets in the emulsion requires relatively greater energy for smaller droplets. As a result the fraction of smaller droplets will last longer than those of larger droplets. Thus, for a prediction of the amount of remaining emulsion, information about the amount of smaller droplets is the most important. By adapting the intensity of demulsification to the size of the fraction of small droplets the intensity can be made effective in a way that is tailored to oil/water mixture.

In another embodiment demulsification control module 26 may use the estimated average droplet size to control variation of the intensity of emulsion reduction measures. In many cases the variation of average droplet size is strongly correlated with variations of the number of small droplets. In another example, an estimated x-percentile size may be used. The x-percentile size may be defined in terms of the cumulative distribution, of which the droplet size distribution is the derivative as a function of droplet size, and which expresses the fraction of droplets below a threshold size as a function of the threshold size. The x-percentile size is the threshold size at which the cumulative distribution assumes the value x (x=0.05 for example).

In an embodiment demulsification control module 26 uses the frequency dependent estimation of the attenuation coefficient measurement to estimate selectively the concentration of small droplets and to control emulsion reduction measures dependent on that concentration. An indication of the concentration of small droplets may be estimated by detecting a part of the attenuation that occurs in a predetermined frequency band and integrating (or summing) this part as a function of height. Alternatively, a droplet size distribution may be solved from the frequency dependent attenuation coefficient $A(f;h)$ as a function of height by means of the relation between droplet size distribution $N(d;h)$ as a function of height (d being the droplet diameter), according to $$A(f;h) = \text{Sum } N(d;h) * A(f;d)$$

The sum (or an integral being taken over the diameters). This relation may be inverted by assuming that the size distribution can be described by some parameterized function $g(d;b(h))$ such as a Gaussian, wherein the parameters b may comprise the amplitude, average and standard deviation of the size distribution as a function of height. In this case values of the parameters may be selected that lead to a frequency dependence of the attenuation coefficient $A(f;h)$ that best fits measured path attenuations.

Next a control parameter for emulsion reduction may be derived from the parameters, for example as a fraction of droplets in a predetermined size range, a weighted sum (or integral) of the distribution $N(d;h)$ weighted according to diameter d. Demulsification control module 26 may be configured to increase and decrease the intensity of emulsion reduction measures automatically in response to increases and decreases of this control parameter. Alternatively, e.g. when the measured properties vary only slowly, a human operator may use the results to adjust emulsion reduction measures.

The variation of the intensity of emulsion reduction measures may be applied to a basic intensity of emulsion reduction measures, in terms of a basic flow speed, a basic rate of adding demulsifying agent, basic heating power etc. The control measures to realize the basic intensity may be set to an initial value manually. In addition the basic intensity may be set according to properties of the oil water mixture that have been measured in other ways or do not change significantly, for example an overall oil/water ratio. The basic intensity may be increased and decreased with the height (h3–h1) of emulsion, if it does not extend over the entire liquid part of the fluid.

Demulsification control module 26 may comprise a stored table of control values of emulsion reduction measures for different parameter values of the droplet size distribution and optionally emulsion height. This numerical relation may also be realized by providing and using arithmetic functions that relate the measured parameter values to control values. The optimal numerical relation between the selection of control values of emulsion reduction measures and droplet size and optionally height depends on the properties of separator vessel, its operational parameter and the type of demulsification measure used. This relation can be determined in a calibration step, for subsequent use, by determining values of a proposed control parameter that is derived from droplet size distribution measured in the calibration step, applying different intensities of demulsification and testing the resulting height of the emulsion at weir 10b. A lowest intensity that substantially makes the height zero can then be assigned to the measured value of the control parameter, for application during subsequent control. In the embodiment the calibration may involve a feedback loop to control demulsification control module 26 to regulate the emulsion height near weir 10*b* to a threshold value. In this embodiment feed forward steering values as a function of droplet size may be determined by copying intensities of demulsification measures that result from feedback when different droplet sizes are measured.

In a fifth step 35 weir control module 24 controls weir height. In an embodiment weir height is controlled dependent on the estimated parameters upstream of demulsification. From the measured oil/water ratio as a function of height, control module 24 may compute a predicted height of the separation between the oil and water bodies after demulsification. Control module 24 may use this predicted height to control weir 10*b*.

Figure 8:
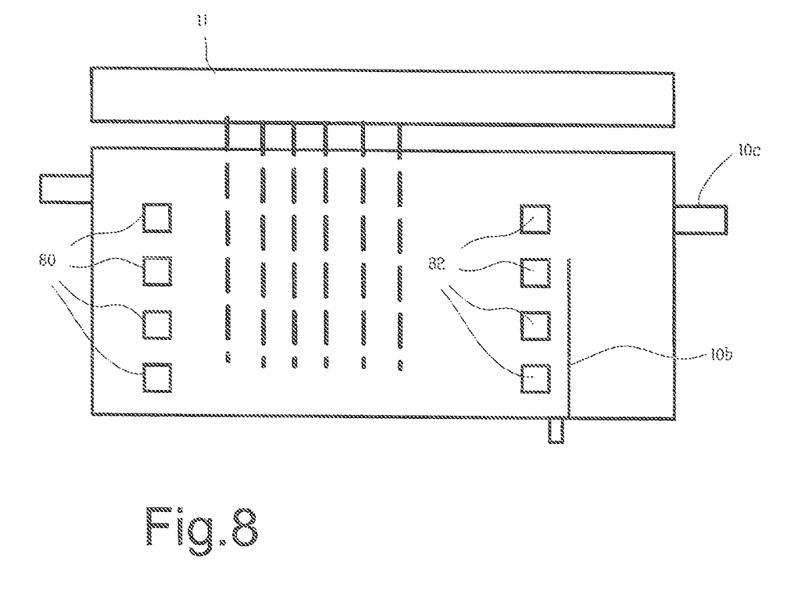
FIG. 8 shows a separator with a plurality of sets of transducers

FIG. 8 shows an embodiment with a first and second set of transducers 80, 82 at respective different stages along the flow direction (different stages being characterized by different x-position, i.e. coordinate in the flow direction) in separator 10. Stages adjacent the inlet of separator 10 and weir 84 will be called an upstream stage and a downstream stage respectively. In this embodiment, signal processing module 22 (not shown) may be configured to estimate parameters of the fluid at each of the respective stages. The estimate of attenuation coefficients from the upstream location may be used to control the intensity of emulsion reduction and estimated heights may be used to control the height of weir 84. In addition the estimated obtained from the downstream location may be used in a feedback control of demulsification. In this case additional control based on the upstream estimation help to reduce the range of variations that need to be controlled in the feedback control and the variations that occur before feedback is effective.

When it is detected at the downstream stage that a height of emulsion remains at the stage of weir 10*b*, the control of the height of weir 10*b* may be adapted to the height of the emulsion. In an embodiment wherein separator is used to separate waste water substantially without oil, weir control module 24 may be configured to control weir height dependent on the computed height h1 of the water-emulsion interface, so that all of the fluid in separator 10 above this height passes over the weir. In another embodiment, wherein separator 10 is used to separate oil substantially without water, weir control module 24 may be configured to control weir height dependent on the computed height h2 of the emulsion-oil interface, so that only of the fluid in separator 10 above this height passes over the weir.

Although embodiments with a horizontal separator with height variable weir have been shown by way of example, it should be understood that alternatively other types of separator may be used, such as a vertical separator from which oil and water are let out at respective levels and an emulsion is introduced between these levels. In this case flow speed may be controlled dependent on the measured heights and the intensity and/or height of emulsion reduction measures may be controlled dependent on the measured attenuation as a function of height.

Although embodiments have been shown wherein transducers are used at a stage upstream of demulsification, to control the intensity of demulsification, it should be appreciated that in another embodiment use of upstream transducers may be omitted. When the emulsion properties vary only slowly feedback control of demulsification may suffice.

Measurement control module 20, signal processing module 22, weir control module 24 and demulsification control module 26 may be implemented using a programmable processing circuit and software with instructions for the programmable circuit, designed to perform the functions of these modules. The programmable processing circuit may comprise a single computer to execute instructions for all modules, or a plurality of processors to implement different ones of the modules. Part or all of the modules may be logic circuits designed specifically to perform the described functions. As used herein statements that the modules are configured to perform specified functions covers both such dedicated logic circuits with a circuit design to perform the functions and implementation using a programmable processing circuit with a program to make the processing circuit perform these functions.

Although an application to separation of an oil water mixture has been described, it should be appreciated that similar ultrasound techniques can be applied measure the properties of other liquid mixtures and to control their demulsification and separation.

As will be appreciated, the use of measurements of signal transmission between transducers at different heights makes it possible to determine properties like the speed of sound in the separator as a function of height with a greater resolution than the distance between the heights of successive transducers. Deviations from linear interpolation of the speed of sound between the heights of different transducers can be determined and heights h1, h3 of interfaces can be determined with greater resolution than the distance between the heights of different transducers. Thus, the same resolution can be obtained with a smaller number transducers than with a larger number of transducers that are used only to measure transmission at individual heights. Interface levels can be detected that do not show as discrete steps in the speed of sound.

Although pairs of transducers at equal heights on horizontally opposite sides of separator may be provided, as shown, it should be appreciated that such pairs at equal height are not indispensible. By determining the parameters of the model that predict the measured travel times between pairs of transducers, a high resolution height dependence can be determined also if there are no transducers at equal heights.

As will be appreciated, the use of measurements of frequency dependent path attenuations between transducers at equal heights in combination with frequency dependent path attenuations between transducers at different heights makes it possible to determine the attenuation coefficients in the separator as a function of height with a greater resolution than the distance between the heights of successive transducers. Deviations from linear interpolation of the attenuation coefficients between the heights of different transducers can be determined and heights h1, h2, h3 of interfaces can be determined with greater resolution than the distance between the heights of different transducers. Thus information can be determined of a type that can be used to control the intensity of emulsion reduction measures. At least part of this information is difficult it not impossible to determine from travel times. The same resolution can be obtained with a smaller number transducers than with a larger number of transducers that are used only to measure transmission at individual heights.

Although this is true when pairs of transducers at equal heights on horizontally opposite sides of separator are provided, it should be appreciated that such pairs at equal height are not indispensible for this either. By determining the parameters of the model that predict the measured path attenuations between pairs of transducers, a high resolution height dependence can be determined also if there are no transducers at equal heights.

Although embodiments have been shown with equal numbers of transducers on both sides, it should be appreciated that this does not mean that it is necessary that each transducer on one side is used only in combination with one transducer on the other side. Response signals to transmission from a transducer on one side may be measured at a plurality of transducers on the other side and vice versa. Typically, each transducer has an associated limited opening angle, defining a range of positions of possible transducers on the wall of the vessel from which it is able to receive, or to which it is able to transmit, ultrasound signals. In an embodiment at least one transducer has an opening angle that contains the positions of a plurality of other transducers. In this embodiment, transmitted signals between this at least one transducer and the plurality of other transducers may be used in the determination of the height dependence of transmission properties.

It may be noted that in each case received signals (and optionally travel time and/or path attenuation) are measured between transducers of which the line of connection between the transducers has a horizontal component. Thus at least partly horizontal transmission effects are determined. By using lines of connection at a plurality of angles to the horizontal a higher resolution is obtained than would be possible with the same number of transducers if only horizontal transmission was used.

The invention claimed is:

1. A method of monitoring operation of a liquid mixture separator, the separator comprising a vessel through which a mixture of different liquid components flows in a horizontal direction, the separator comprising a plurality of ultrasound transducers on a wall of the vessel at different heights at a common horizontal position along the horizontal direction, the method comprising
transmitting ultrasound through the vessel from at least first part of the transducers and detecting ultrasound arriving at at least a second part of the transducers for a plurality of ultrasound wavelengths, including detecting a combination of response signals measured for ultrasound ray paths at mutually different angles to the horizontal, and between transducers of the first part and transducers of the second part at mutually different heights;
fitting parameter values of a model that relates a parameter of a height dependent droplet size distribution to the detected combination of response signals.

2. A method according to claim 1, comprising automatically controlling application of demulsification measures to the liquid mixture in the vessel dependent on a fitted value of the parameter of the height dependent droplet size distribution.

3. A method according to claim 2, comprising selecting between applying different demulsification measures or different combinations of demulsification measures dependent on said fitted value of the parameter of the height dependent droplet size distribution.

4. A method according to claim 2, comprising selecting an intensity of the demulsification measures dependent on said fitted value of the parameter of the height dependent droplet size distribution.

5. A method according to claim 2, comprising selecting a height dependence of the demulsification measures dependent on said fitted value of the parameter of the height dependent droplet size distribution.

6. A method according to claim 2, wherein said common horizontal position is located along the horizontal direction and upstream of a further horizontal position at which the demulsification measures are applied, feed-forward control being used to control the application of the demulsification measures.

7. A method according to claim 1, wherein the parameter values of the model include at least one parameter defining a liquid component ratio gradient, between corresponding pure bodies of the different liquid components.

8. A method according to claim 7, wherein model fitting comprises determining ultrasound ray paths with non-zero curvature dependent on the liquid component ratio gradient.

9. A method according to claim 7, wherein the parameters of the model include at least one parameter defining a transition height between an oil droplet in water emulsion and a water droplet in oil emulsion, the model providing for a discontinuity in the ultrasound wavelength dependent transmission properties at said transition height.

10. The method of claim 7, wherein the liquid component ratio gradient is an oil-water ratio gradient.

11. The method of claim 7, wherein the pure bodies of the different liquid components are an oil body and a water body.

12. The method of claim 1, wherein a space within the vessel for the liquid mixture is located between the first part of the transducers and the second part of the transducers.

13. The method of claim 1, wherein the liquid mixture separator is an oil-water separator.

14. A liquid mixture separator, comprising
a separation vessel;
a plurality of ultrasound transducers on a wall of the vessel at different heights at a common horizontal position along a horizontal direction of flow;
an ultrasound measurement control module coupled to the transducers, configured to cause ultrasound at a plurality of wavelengths to be transmitted through the separation vessel, from a first part of the transducers and to cause a combination of response signals to be detected by a second part of the transducers, the combination of response signals being measured for ultrasound ray paths at mutually different angles to the horizontal, and between transducers of the first part and transducers of the second part at mutually different heights;
a signal processing module coupled to the transducers, the signal processing module being configured to fit parameter values of a model that relates a parameter of height dependent droplet size distribution to the detected combination of response signals.

15. A liquid mixture separator according to claim 14, comprising
controllable emulsion reducer that is operational in the separation vessel and
a demulsification control module, the demulsification control module being configured to control the emulsion reducer dependent on a fitted value of said height dependent droplet size distribution.

16. A liquid mixture separator according to claim 15, wherein said common horizontal position is located upstream of a further horizontal position along the horizontal direction wherein the emulsion reducer is operational.

17. A liquid mixture separator according to claim 15, wherein the controllable emulsion reducer is configured to apply selectable ones or selectable combinations of emulsion reduction measures in the separation vessel, the demulsification control module being configured to control selection of the emulsion reduction measures dependent on the fitted value of said height dependent droplet size distribution.

18. A liquid mixture separator according to claim 15, wherein the controllable emulsion reducer is configured to apply at least one emulsion reduction measure with a selectable height dependence in said vessel, the demulsification control module being configured to control selection of the height dependence dependent on the fitted value of said height dependent droplet size distribution.

19. A liquid mixture separator according to claim 14, wherein the vessel has a rounded cross-section at said common horizontal position, the transducers being clamped onto an exterior wall of the vessel, at least part of the transducers being configured to transmit ultrasound at respective transmission angles through the vessel that are different from the horizontal direction of flow.

20. The liquid mixture separator of claim 14, wherein a space within the vessel for the liquid mixture is located between the first part of the transducers and the second part of the transducers.

21. The liquid mixture separator of claim 14, which is an oil-water separator.

\* \* \* \* \*